United States Patent [19]

Robinson

[11] Patent Number: 4,943,632

[45] Date of Patent: Jul. 24, 1990

[54] CEFTAZIDIME DIHYDROCHLORIDE FORMIC ACID SOLVATES

[75] Inventor: Colin Robinson, Ulverston, England

[73] Assignee: Glaxo Group Limited, London, United Kingdom

[21] Appl. No.: 305,541

[22] Filed: Feb. 3, 1989

[30] Foreign Application Priority Data

Feb. 5, 1988 [GB] United Kingdom ............... 8802622

[51] Int. Cl.$^5$ .......................................... C07D 501/46
[52] U.S. Cl. ..................................................... 540/225
[58] Field of Search ................... 540/225, 222, 227; 514/206

[56] References Cited

U.S. PATENT DOCUMENTS

| | | | |
|---|---|---|---|
| 4,258,041 | 3/1981 | O'Callaghan | 424/246 |
| 4,329,453 | 5/1982 | Brodie et al. | 546/25 |
| 4,467,086 | 8/1984 | Miller | 546/25 |
| 4,537,959 | 8/1989 | Chou | 544/25 |

FOREIGN PATENT DOCUMENTS 166580 2/1986 European Pat. Off. .
2132616 7/1984 United Kingdom .

OTHER PUBLICATIONS

Chemical Abstracts, vol. 105, 30045x (1986).
Chemical Abstracts, vol. 109, 170117e (1988).

*Primary Examiner*—Nicholas S. Rizzo
*Attorney, Agent, or Firm*—Bacon & Thomas

[57] ABSTRACT

The invention relates to the crystalline formic acid solvate of (6R, 7R)-7-[(Z)-2-(2-Aminothiazol-4-yl)-2-(2-carboxyprop-2-oxyimino)acetamido]-3-(1-pyridiniummethyl)ceph-3-em-4-carboxylate dihydrochloride (ceftazidime dihydrochloride).

The crystalline solvate is a useful intermediate in the preparation of forms of ceftazidime suitable for administration, e.g. the pentahydrate.

10 Claims, No Drawings

CEFTAZIDIME DIHYDROCHLORIDE FORMIC ACID SOLVATES

The present invention relates to an intermediate of value in the synthesis of the cephalosporin antibiotic ceftazidime. More particularly the invention relates to the formic acid solvate of the dihydrochloride of ceftazidime in crystalline form and to processes for preparing this solvate and to a process for converting the solvate into ceftazidime e.g. in the form of the pentahydrate.

Ceftazidime, (6R,7R)-7-[(Z)-2-(2-aminothiazol-4-yl)-2-(2-carboxyprop-2-oxyimino)acetamido]-3-(1-pyridiniummethyl)ceph-3-em-4-carboxylate is described in UK Patent Specification No. 2025398 and has the following formula:

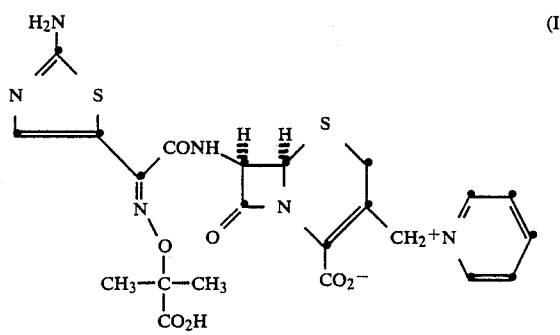

Ceftazidime is an effective antibiotic agent with high activity against a broad spectrum of Gram-positive and Gram-negative bacteria and the compound possesses high stability to a wide range of bacterial $\beta$-lactamases.

Solvates and non-toxic salts of ceftazidime, for example base salts and acid addition salts, are also generally disclosed in UK Patent Specification No. 2025398 including the dihydrochloride in an amorphous form. The dihydrochloride i.e. the bishydrochloride of ceftazidime in crystalline form is specifically described in UK Patent Specification No. 2064513.

UK Patent Specification No. 2063871 describes the preparation and isolation of ceftazidime in the form of a crystalline pentahydrate. This pentahydrate has a well-defined crystalline structure and is stable at elevated temperatures for an extended period of time. It is thus of particular value in pharmaceutical use.

Ceftazidime pentahydrate may be conveniently prepared by the conversion of ceftazidime dihydrochloride into the crystalline ceftazidime pentahydrate as described in UK Specification No. 2063871.

In order to improve the efficiency of the process for preparing ceftazidime it is advantageous to have intermediates which are readily prepared and are obtained in a high degree of purity. The present invention provides such an intermediate namely the formic acid solvate of ceftazidime dihydrochloride in crystalline form.

Thus according to one aspect of the present invention we provide (6R,7R)-7-[(Z)-2-(2-aminothiazol-4-yl)-2-(2-carboxyprop-2-oxyimino)acetamido]-3-(1-pyridiniummethyl)ceph-3-em-4-carboxylate dihydrochloride in the form of a crystalline formic acid solvate.

This new crystalline solvate of ceftazidime dihydrochloride may be prepared with a high degree of purity, substantially free from amorphous salts and/or amorphous solvates of ceftazidime, and the product has operational advantages in handling over unsolvated material. Use of the unsolvated form involves a rather difficult drying process. This factor is substantially obviated by using the crystalline solvate of the present invention. The new solvated form which is consistently obtained in high yield in crystalline form filters readily and can easily be washed and dried. These properties of the crystalline formic acid solvate render it of particular value as an intermediate in the synthesis of ceftazidime.

The crystalline formic acid solvate of ceftazidime dihydrochloride has been characterised by its infra-red and/or X-ray powder diffraction pattern (for details of the methods used, see the Examples section).

IR Spectrum: $\nu$ max (Nujol)—3368, 3175, 1775, 1731, 1680, 1541, 1500, 1411, 1203, 1190, 1150, 1134, 1014, 997, 753, 671 and 597 cm$^{-1}$.

X-ray Diffraction Pattern (given as d spacings in Angstrom units and percentage intensities I)

| d | I | d | I | d | I |
|---|---|---|---|---|---|
| 12.49 | 3.4 | 4.08 | 21.4 | 2.42 | 3.0 |
| 10.25 | 4.2 | 3.92 | 65.2 | 2.35 | 5.5 |
| 9.54 | 5.1 | 3.67 | 23.0 | 2.31 | 3.1 |
| 8.47 | 38.2 | 3.57 | 13.0 | 2.25 | 10.2 |
| 7.64 | 3.5 | 3.47 | 7.5 | 2.20 | 2.0 |
| 7.35 | 6.3 | 3.36 | 6.6 | 2.12 | 6.5 |
| 6.91 | 6.1 | 3.27 | 25.8 | 2.09 | 4.0 |
| 6.29 | 22.8 | 3.22 | 16.6 | 2.03 | 4.9 |
| 5.93 | 2.3 | 3.15 | 3.4 | | |
| 5.77 | 8.4 | 3.12 | 4.2 | | |
| 5.51 | 13.4 | 3.05 | 13.3 | | |
| 5.37 | 12.8 | 2.88 | 2.9 | | |
| 5.10 | 4.7 | 2.81 | 6.6 | | |
| 4.93 | 78.9 | 2.73 | 7.3 | | |
| 4.86 | 2.2 | 2.68 | 5.4 | | |
| 4.68 | 6.5 | 2.62 | 12.3 | | |
| 4.35 | 100.0 | 2.58 | 5.6 | | |
| 4.26 | 40.0 | 2.46 | 2.9 | | |

The crystalline formic acid solvate of ceftazidime dihydrochloride may be prepared conveniently from a solution of ceftazidime dihydrochloride containing formic acid.

Thus, according to a further embodiment of the invention we provide a process for preparing the desired crystalline formic acid solvate of ceftazidime dihydrochloride with the above characterising data by crystallisation from a solution of ceftazidime dihydrochloride containing formic acid. In particular this may be effected by addition of, or mixing with, an organic counter solvent to the formic acid solution of ceftazidime dihydrochloride. The product may be isolated and dried in a conventional manner.

The organic counter solvent enhances the crystallisation of the formic acid solvate and may be an alcohol, for example ethanol or isopropanol, a ketone, for example acetone, or an ether, for example diethyl ether, di-isopropylether, dioxan or tetrahydrofuran. A mixture of solvents may be employed or two or more counter solvents may be added sequentially to the crystallisation medium.

The crystallisation may be effected at a temperature within the range 0° to 60° C. and conveniently 10° to 40° C., for example in the range 25° to 35° C., preferably followed by a step of cooling to a temperature within the range 0° to 10° in order to enhance the yield. Crystallisation may be aided by seeding the crystallisation medium for example with crystals of the desired formic acid solvate or of unsolvated crystalline ceftazidime dihydrochloride.

The product may be isolated in any convenient manner, for example by filtration, decantation or centrifugation and dried in any conventional way, for example in vacuo at 15° to 40° C.

The ceftazidime dihydrochloride for use in the preparation of the new crystalline formic acid solvate according to the invention may be prepared by procedures disclosed in UK Patent Specification Nos. 2064513, 2025398 and 2132616. The dihydrochloride may be in isolated form and then dissolved in formic acid or may, according to a preferred procedure, be formed in formic acid solution without isolation.

Thus, for example, as described in UK Patent Specification Nos. 2064513 and 2025398 a protected intermediate (6R,7R)-7-[(Z)-2-(2-triphenylmethylaminothiazol-4-yl)-2-(2-t-butoxycarbonylprop-2-oxyimino)acetamido]-3-(1-pyridiniummethyl)ceph-3-em-4-carboxylate or a solvate thereof may be subjected to deprotection in formic acid containing hydrochloric acid whereby, after removal of precipitated triphenylcarbinol, ceftazidime dihydrochloride can be isolated in solid form.

The procedure described in UK Patent Specification No. 2025398 for isolating the ceftazidime dihydrochloride is not particularly convenient for large scale production and furthermore the product so obtained is amorphous. A more convenient procedure for isolating the ceftazidime dihydrochloride is described in UK Patent Specification No. 2064513 but when this procedure is adapted for use on an industrial scale, the ceftazidime dihydrochloride so produced is generally predominantly amorphous unless recrystallized. We have now found that by seeding the formic acid solution of ceftazidime dihydrochloride with the crystalline ceftazidime dihydrochloride formic acid solvate or by adjustment of the proportion of counter solvent ceftazidime dihydrochloride formic acid solvate can be caused to crystallise in high yield and purity. This avoids the need for a separate recrystallisation step where it is desired to produce a crystalline intermediate having the advantages of ease of filtration, handling and drying.

In general it has been found that the crystalline ceftazidime dihydrochloride formic acid solvate is purer in terms of unwanted impurities than amorphous ceftazidime dihydrochloride produced as described above.

The formic acid solvate of ceftazidime dihydrochloride prepared by the methods described above may crystallise as a partial hydrate and the degree of solvation and hydration may vary depending upon the precise reaction conditions employed. This may lead to slight variation in the stoichiometry of formic acid solvate. The percentage of formic acid in the crystalline product may thus vary between, for example, 6.5 and 8.0% by weight, although being preferably about 6.9% by weight. Accordingly the present invention includes within its scope all hydrated crystalline formic acid solvates of ceftazidime dihydrochloride with the characterising data herein defined.

The formic acid solvate of ceftazidime dihydrochloride provided by this invention may be employed to produce ceftazidime for example in the form of the pentahydrate using the process of crystallisation from aqueous solution described in UK Patent Specification No. 2063871.

The following examples are given by way of illustration only and are not limiting.

In the Examples temperatures are expressed in degrees celsius. Water content was determined by the Karl Fischer method. Nujol is a trade mark.

EXAMPLE 1

Ceftazidime dihydrochloride, formic acid solvate

Crystalline solid ceftazidime dihydrochloride (25 g) as prepared in UK Patent Specification No. 2064513 was dissolved in formic acid (98–100% w/w, 50 ml) at 20°. To this clear, well stirred solution at 10° to 15° was added, over 15 minutes, acetone (150 ml). The solution temperature was raised to 35° and crystallisation was initiated by scratching. The slurry was stirred for 1 hour at 35°. Crystallisation was completed by successive additions of acetone (302 ml) over 20 minutes and di-isopropyl ether (230 ml) over 10 minutes. The mixture was stirred at 35° for a further hour and then cooled to 5°. The product was filtered, washed with acetone (2×80 ml slurry, 1×60 ml displacement) and dried in vacuo at 35° to give the title compound as a crystalline solid (25.55 g).

Formic acid content 7.3% w/w
Water content 0.3%
Purity based on a water and solvent free basis 98.5%.

EXAMPLE 2

Ceftazidime dihydrochloride, formic acid solvate

To a stirred slurry of the DMF solvate of (6R,7R)-7-[(Z)-2-(2-triphenylmethylaminothiazol-4-yl)-2-(2-t-butoxycarbonylprop-2-oxyimino)acetamido]-3-(1-pyridiniummethyl)ceph-3-em-4-carboxylate (50 g) in formic acid (98–100% w/w, 92 ml) held below 28° was added concentrated hydrochloric acid (21 ml) over 30 minutes. During the addition and the subsequent 1 hour 50 minutes reaction period the temperature of the mixture was held below 28°. The precipitated triphenyl carbinol was removed by filtration and washed with formic acid (2×14.5 ml). The combined filtrate and washes were cooled to 15° and acetone (638 ml) was added over 20 minutes to the well stirred mixture. The resulting clear solution was heated to 35° with a crystalline seed (0.2 g) of ceftazidime dihydrochloride formic acid solvate being added when the solution temperature had reached 25°. The crystallising mixture was stirred for 1 hour at 35° and then acetone (302 ml) was added over 15 minutes followed by di-isopropyl ether (230 ml) over 10 minutes. The mixture was stirred for a further hour at 35° then cooled to 5°. The product was filtered, washed with acetone (2×80 ml slurry, 1×60 ml displacement) and dried in vacuo at 35° to give the title compound as a crystalline solid (30.27 g).

Formic acid content 6.7%
Water content 0.7%
Purity on a water and solvent free basis 96.8%

EXAMPLE 3

Ceftazidime dihydrochloride, formic acid solvate

To a stirred slurry of the DMF solvate of (6R,7R)-7-[(Z)-2-(2)-triphenylmethylaminothiazol-4-yl)-2-(2-t-butoxycarbonylprop-2-oxyimino)acetamido]-3-(1-pyridiniummethyl)ceph-3-em-4-carboxylate (50 g) in formic acid (98–100% w/w, 92 ml) held below 28° was added concentrated hydrochloric acid (21 ml) over 30 minutes. During the addition and the subsequent 1 hour 50 minutes reaction period the temperature of the mixture was held below 28°. The precipitated triphenyl carbinol was removed by filtration and washed with formic acid (2×14.5 ml). The combined filtrate and washes were cooled to 15° and acetone (520 ml) was added over 20 minutes to the well stirred mixture. The resulting clear solution was heated to 35° with a crystalline seed (0.2 g) of ceftazidime dihydrochloride being added when the solution temperature had reached 25°. The crystallising mixture was stirred for 1 hour at 35° and then acetone (302 ml) was added over 15 minutes followed by di-isopropyl ether (230 ml) over 10 minutes. The mixture was stirred for a further hour at 35° then cooled to 5°. The product was filtered, washed with acetone (2×80 ml slurry, 1×60 ml displacement) and dried in vacuo at 35° to give the title compound as a crystalline solid (29.53 g).

Formic acid content 7.7%
Water content 0.3%
Purity on a water and solvent free basis 97.4%

Typical infra red and X-ray diffraction spectra for the formic acid solvate of ceftazidime dihydrochloride prepared as in Examples 1 to 3 are as follows:

IR Spectrum: $\nu$ max (Nujol)—3368, 3175, 1775, 1731, 1680, 1541, 1500, 1411, 1203, 1190, 1150, 1134, 1014, 997, 753, 671 and 597 cm$^{-1}$.

X-ray Diffraction Pattern (given as d spacings in Angstrom units and percentage intensities I)

| d | I | d | I | d | I |
|---|---|---|---|---|---|
| 12.49 | 3.4 | 4.08 | 21.4 | 2.42 | 3.0 |
| 10.25 | 4.2 | 3.92 | 65.2 | 2.35 | 5.5 |
| 9.54 | 5.1 | 3.67 | 23.0 | 2.31 | 3.1 |
| 8.47 | 38.2 | 3.57 | 13.0 | 2.25 | 10.2 |
| 7.64 | 3.5 | 3.47 | 7.5 | 2.20 | 2.0 |
| 7.35 | 6.3 | 3.36 | 6.6 | 2.12 | 6.5 |
| 6.91 | 6.1 | 3.27 | 25.8 | 2.09 | 4.0 |
| 6.29 | 22.8 | 3.22 | 16.6 | 2.03 | 4.9 |
| 5.93 | 2.3 | 3.15 | 3.4 | | |
| 5.77 | 8.4 | 3.12 | 4.2 | | |
| 5.51 | 13.4 | 3.05 | 13.3 | | |
| 5.37 | 12.8 | 2.88 | 2.9 | | |
| 5.10 | 4.7 | 2.81 | 6.6 | | |
| 4.93 | 78.9 | 2.73 | 7.3 | | |
| 4.86 | 2.2 | 2.68 | 5.4 | | |
| 4.68 | 6.5 | 2.62 | 12.3 | | |
| 4.35 | 100.0 | 2.58 | 5.6 | | |
| 4.26 | 40.0 | 2.46 | 2.9 | | |

The crystalline sample was loaded into a 0.3 mm diameter glass capillary and photographed by the Debye-Scherrer method in a 114.6 mm diameter camera by exposure for 3 hours to CuK$\alpha$ radiation.

EXAMPLE 4

Ceftazidime dihydrochloride, formic acid solvate (20 g) was dissolved in water (40 ml) and the solution adjusted to pH6 with 2N sodium hydroxide solution (55 ml). The solution was treated with charcoal (0.5 g) for 10 min and the charcoal removed by filtration, washed with water (20 ml) and the washes combined with the filtrate. The pH of the bulked solution was adjusted to 4.2 with 3N sulphuric acid (8 ml) and the mixture seeded with ceftazidime pentahydrate. The mixture was then further adjusted to pH 3.7 with 3N sulphuric acid, cooled to 5° and filtered. The product was washed with water, then acetone and dried at ambient temperature in an air oven to give the title compound as a crystalline solid (15.93 g).

Water content 13.8%
Formic acid content 0.02%
Purity based on a water and solvent free basis 98.0%.

I claim:

1. (6R,7R)-7-[(Z)-2-(2-Aminothiazol-4-yl)-2-(2-carboxyprop-2-oxyimino)acetamido]-3-(1-pyridiniummethyl)ceph-3-em-4-carboxylate dihydrochloride (ceftazidime dihydrochloride) in the form of a crystalline formic acid solvate.

2. The crystalline ceftazidime dihydrochloride formic acid solvate of claim 1 which exhibits substantially the following infra-red spectrum in Nujol: $\nu$max—3368, 3175, 1775, 1731, 1680, 1541, 1500, 1411, 1203, 1190, 1150, 1134, 1014, 997, 753, 671 and 597 cm$^{-1}$.

3. The crystalline ceftazidime dihydrochloride formic acid solvate of claim 1 which exhibits substantially the following X-ray diffraction pattern, expressed as d spacings and relative intensities:

| d | I | d | I | d | I |
|---|---|---|---|---|---|
| 12.49 | 3.4 | 4.08 | 21.4 | 2.42 | 3.0 |
| 10.25 | 4.2 | 3.92 | 65.2 | 2.35 | 5.5 |
| 9.54 | 5.1 | 3.67 | 23.0 | 2.31 | 3.1 |
| 8.47 | 38.2 | 3.57 | 13.0 | 2.25 | 10.2 |
| 7.64 | 3.5 | 3.47 | 7.5 | 2.20 | 2.0 |
| 7.35 | 6.3 | 3.36 | 6.6 | 2.12 | 6.5 |
| 6.91 | 6.1 | 3.27 | 25.8 | 2.09 | 4.0 |
| 6.29 | 22.8 | 3.22 | 16.6 | 2.03 | 4.9 |
| 5.93 | 2.3 | 3.15 | 3.4 | | |
| 5.77 | 8.4 | 3.12 | 4.2 | | |
| 5.51 | 13.4 | 3.05 | 13.3 | | |
| 5.37 | 12.8 | 2.88 | 2.9 | | |
| 5.10 | 4.7 | 2.81 | 6.6 | | |
| 4.93 | 78.9 | 2.73 | 7.3 | | |
| 4.86 | 2.2 | 2.68 | 5.4 | | |
| 4.68 | 6.5 | 2.62 | 12.3 | | |
| 4.35 | 100.0 | 2.58 | 5.6 | | |
| 4.26 | 40.0 | 2.46 | 2.9 | | |

4. Crystalline ceftazidime dihydrochloride formic acid solvate as claimed in claim 1 substantially free from amorphous ceftazidime salts and/or solvates which filters readily and can be easily washed and dried.

5. A process for preparing a crystalline ceftazidime dihydrochloride formic acid solvate as claimed in claim 1 which comprises crystallisation of the said solvate from a solution of ceftazidime dihydrochloride containing formic acid.

6. A process as claimed in claim 5 wherein crystallisation is effected by mixing a formic acid solution of ceftazidime dihydrochloride with an organic counter solvent.

7. A process as claimed in claim 5 wherein crystallisation is effected by addition of a seed crystal of ceftazidime dihydrochloride formic acid solvate.

8. A process as claimed in claim 6 where crystallisation is effected by addition of a seed crystal of ceftazidime dihydrochloride formic acid solvate.

9. A process as claimed in claim 5 wherein the solution of ceftazidime dihydrochloride in formic acid is prepared by deprotection of (6R,7R)-7-[(Z)-2-(2-triphenylmethylaminothiazol-4-yl)-2-(2-t-butoxycarbonylprop-2-oxyimino)acetamido]-3-(1-pyridiniummethyl)ceph-3-em-4-carboxylate or a solvate thereof in solution in formic acid containing sufficient hydrochloric acid to form said dihydrochloride.

10. A process as claimed in claim 5 in which the ceftazidime dihydrochloride formic acid solvate so produced is used to prepare crystalline ceftazidime pentahydrate.

* * * * *